(12) United States Patent
Rezach

(10) Patent No.: US 8,298,275 B2
(45) Date of Patent: Oct. 30, 2012

(54) DIRECT CONTROL SPINAL IMPLANT

(75) Inventor: William Alan Rezach, Atoka, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 426 days.

(21) Appl. No.: 12/609,745

(22) Filed: Oct. 30, 2009

(65) Prior Publication Data

US 2011/0106174 A1 May 5, 2011

(51) Int. Cl.
*A61B 17/86* (2006.01)
*A61B 17/70* (2006.01)

(52) U.S. Cl. ........ 606/308; 606/305; 606/306; 606/328; 606/307; 606/267; 606/269; 606/270

(58) Field of Classification Search .......... 606/256–257, 606/266–270, 305–308, 319–321, 328
See application file for complete search history.

(56) References Cited

U.S. PATENT DOCUMENTS

| | | | |
|---|---|---|---|
| 4,946,458 A | 8/1990 | Harms et al. | |
| 5,190,543 A | 3/1993 | Schlapfer | |
| 5,520,689 A | 5/1996 | Schlapfer et al. | |
| 5,536,268 A | 7/1996 | Griss | |
| 5,672,176 A | 9/1997 | Biedermann et al. | |
| 5,989,254 A | 11/1999 | Katz | |
| 6,537,276 B2 | 3/2003 | Metz-Stavenhagen | |
| 6,692,500 B2 | 2/2004 | Reed | |
| 6,736,820 B2 | 5/2004 | Biedermann et al. | |
| 6,800,078 B2 | 10/2004 | Reed | |
| 6,837,889 B2 | 1/2005 | Shluzas | |
| 7,559,943 B2 | 7/2009 | Mujwid | |
| 8,002,806 B2* | 8/2011 | Justis | 606/264 |
| 8,075,599 B2* | 12/2011 | Johnson et al. | 606/266 |
| 2002/0026193 A1 | 2/2002 | Barker et al. | |
| 2004/0225289 A1* | 11/2004 | Biedermann et al. | 606/61 |
| 2005/0154391 A1* | 7/2005 | Doherty et al. | 606/61 |
| 2005/0159750 A1 | 7/2005 | Doherty | |
| 2005/0187548 A1 | 8/2005 | Butler et al. | |
| 2005/0216003 A1* | 9/2005 | Biedermann et al. | 606/61 |
| 2005/0261687 A1 | 11/2005 | Garamszegi et al. | |
| 2005/0277928 A1* | 12/2005 | Boschert | 606/61 |
| 2006/0036244 A1* | 2/2006 | Spitler et al. | 606/61 |
| 2006/0111715 A1* | 5/2006 | Jackson | 606/61 |
| 2006/0155277 A1* | 7/2006 | Metz-Stavenhagen | 606/61 |
| 2007/0043355 A1 | 2/2007 | Bette et al. | |
| 2007/0088357 A1 | 4/2007 | Johnson et al. | |
| 2008/0177260 A1* | 7/2008 | McKinley et al. | 606/60 |

(Continued)

FOREIGN PATENT DOCUMENTS

DE 4107480 9/1992

(Continued)

*Primary Examiner* — Alvin Stewart
*Assistant Examiner* — Julianna N Harvey

(57) ABSTRACT

A bone anchor assembly is provided, which may be used in cervical, thoracic, lumbar or sacral areas of the spine or other orthopedic locations. The anchor assembly includes a bone anchor, a receiver mounted to the bone anchor, a saddle within the receiver, a spacer within the receiver, and an engaging member. The receiver extends along a central longitudinal axis proximally away from the bone anchor. A rod or other elongated connecting element is received in a passage of the receiver in contact with the saddle, and the engaging member engages the connecting element against the saddle, which engages the saddle against the spacer, which in turn engages the proximal head of the bone anchor in the receiver. The orientation of the saddle in the receiver is adjustable to correspond to the orientation of the connecting element relative to the central longitudinal axis of the receiver.

19 Claims, 13 Drawing Sheets

U.S. PATENT DOCUMENTS

| | | |
|---|---|---|
| 2008/0195159 A1 | 8/2008 | Kloss et al. |
| 2008/0306546 A1 | 12/2008 | Zucherman et al. |
| 2009/0076552 A1* | 3/2009 | Tornier .................. 606/264 |
| 2009/0198280 A1* | 8/2009 | Spratt et al. ............ 606/267 |

FOREIGN PATENT DOCUMENTS

| | | |
|---|---|---|
| DE | 4243951 | 7/1994 |
| DE | 19605640 | 8/1997 |
| WO | WO 2009/106733 | 9/2009 |

* cited by examiner

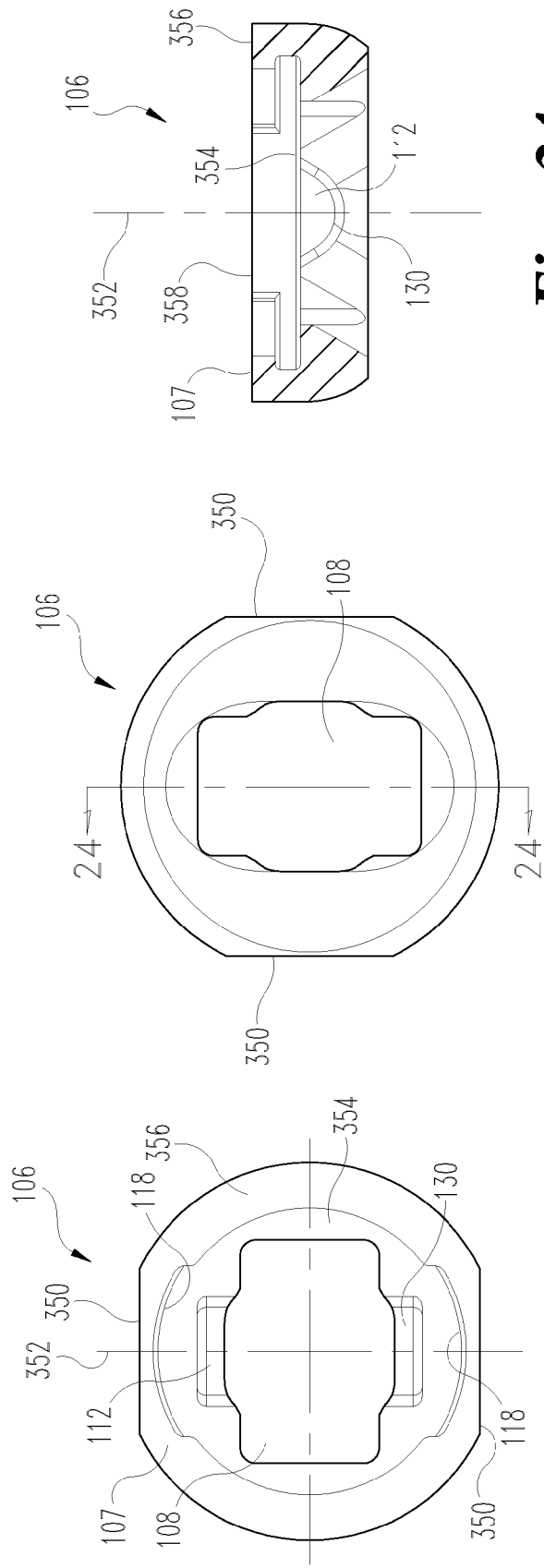

DIRECT CONTROL SPINAL IMPLANT

BACKGROUND

The present invention concerns bone anchors and anchor assemblies, particularly useful for engagement to vertebrae. In a particular embodiment, the invention contemplates a bone anchor assembly with an adjustable saddle to secure an elongate connecting element, such as a spinal rod, along the spinal column.

Several techniques and systems have been developed for correcting and stabilizing the spine and for facilitating fusion at various levels of the spine. In one type of system, an elongated rod is disposed longitudinally along the length of the spine or several vertebrae of the spinal column. The rod may be bent to correspond to the normal or desired curvature of the spine in the particular region being instrumented. For example, the rod can be bent or angled to form a normal kyphotic curvature for the thoracic region of the spine, or a lordotic curvature for the lumbar region. In accordance with such a system, the rod is engaged to various vertebrae along the length of the spinal column by way of a number of fixation elements. A variety of fixation elements can be provided which are configured to engage specific portions of the vertebra. For instance, one such fixation element is a hook that is configured to engage the lamina of the vertebra. Another type of fixation element is a spinal screw which can be threaded into various aspects of the vertebral bone, such as the pedicle.

In one typical procedure utilizing a bendable, angled or linear rod, one or more of the rods is situated on one or both of the opposite sides of the spine or spinous processes. A plurality of bone screws are threadingly engaged to several vertebral bodies, such as to the pedicles of these vertebrae. One or more of the bone screws are maneuvered to manipulate the position or orientation of the vertebral body or bodies to which the bone screw is engaged. The rod(s) are connected or affixed to the plurality of bone screws to apply and maintain corrective and stabilizing forces to the spine.

The bone anchors in spinal procedures can have receivers with channels for the elongated rod or other member that, in some bone anchors, open upward, i.e. directly away from the bone to which the anchor is attached. Other bone anchors utilize channels that open along the medial or lateral side of the anchor to receive the rod. It is desirable in some procedures to utilize a bone anchor where the bone engaging portion of the bone anchor and the receiver are fixed relative to one another so that the forces applied to the receiver are effectively transferred to the vertebra. However, the relative positions of the vertebra and the receiver of the bone anchor may require contouring, bending, and/or angling of the rod through the channel of the bone anchor, which can result in a less than optimal fit between the anchor and the rod, creating undesirable stress concentrations in the rod, bone anchor and/or bony structure. Additional improvements in the bone anchor and rod interface in spinal systems are still needed.

SUMMARY

According to one aspect a bone anchor assembly is disclosed that includes a receiver extending along a central longitudinal axis between a proximal end and an opposite distal end. The receiver includes a distal portion defining a receptacle opening at the distal end and a pair of arms extending from the distal portion along the central longitudinal axis on opposite sides of a passage. A lower outside surface of the receiver includes at least one boss protruding outwardly from the lower outside surface.

Further, a base cap is included that has an upper surface extending to a lower surface, where the lower surface includes a second passage opening into an interior recessed surface in relation to the upper surface. The base cap further includes a lip extending inwardly from the upper surface toward a central axis of the bone cap that defines a passageway between the lip and the recessed surface. The base cap is configured to be connected with a second lower surface of the receiver such that the at least one boss is positioned in the passageway. The interior recessed surface of the base cap includes a head tray. A bone anchor is included that has a distal bone engaging portion and a head at a proximal end of the distal bone engaging portion. The head is configured to be received in the base cap through the second passage when the head is positioned in a first orientation and when the bone anchor is rotated to a second orientation the head is configured to pivotally rest in the head tray.

In another form, a saddle is positioned in the passage of the receiver adjacent to a bottom surface of the receiver. The saddle includes a proximal support surface and a distal surface opposite the proximal support surface. A spacer is positioned in the receptacle between an upper surface of the head of the bone anchor and a lower surface of the saddle. In one form, the spacer includes at least one edge operable to bite into a lower surface of the saddle to secure the saddle in a respective location within the receiver. In yet another form, the saddle is movable in the receiver so that the support surface parallels a longitudinal axis of a connecting element in orientations of the longitudinal axis of the connecting element that vary up to 30 degrees from an orthogonal orientation of the longitudinal axis of the connecting element with the central longitudinal axis of the receiver.

The lip of the base cap can include at least one recessed portion that is operable to allow the at least one boss of the receiver to be positioned within the interior recessed surface of the base cap. Upon rotation of the receiver the at least one boss becomes positioned in the passageway thereby securing the receiver in the base cap. A weld seam may be utilized to further secure the receiver to the base cap.

Another aspect discloses a bone anchor assembly that includes a receiver extending along a central longitudinal axis between a proximal end and an opposite distal end. The receiver includes a distal portion defining a receptacle opening at the distal end and a pair of arms extending from the distal portion along the central longitudinal axis on opposite sides of a passage. The receiver includes a bottom surface extending along the passage between the pair of arms. The passage opens at opposite sides of the receiver between the pair of arms and the receptacle opens into said passage through the bottom surface. A base cap is included that has a second passage located in a central portion of the base cap located in a first orientation and a head tray having two opposing recessed members located in a second orientation in relation to the second passage.

A bone anchor is also included that has a distal bone engaging portion and a head at a proximal end of the distal bone engaging portion. The head is configured to be received in the base cap through the second passage when the head is positioned in the first orientation and when the bone anchor is rotated to the second orientation the head is configured to pivotally rest along a transverse axis in the head tray. A saddle is positioned in the passage of the receiver adjacent to the bottom surface of the receiver. The saddle includes a proximal support surface and a distal surface opposite the proximal support surface. A spacer is positioned between the saddle and the head of the bone anchor inside the receptacle of the receiver.

A connecting element extending along a central longitudinal axis, said connecting element being located in said passage and extending through said opposite sides of said receiver. An engaging member is engaged to the pair of arms to secure the connecting element against the proximal support surface of the saddle. The saddle engages the receiver and is limited to movement in the receiver in a single plane defined by the central longitudinal axis of the receiver and the central longitudinal axis of the connecting element while the bone engaging portion remains in the first orientation.

In one form, the saddle is movable in the receiver so that the support surface parallels the longitudinal axis of the connecting element in orientations of the longitudinal axis of the connecting element that vary up to 30 degrees from an orthogonal orientation of the longitudinal axis of the connecting element with the central longitudinal axis of the receiver. In another form, the pair of arms include inner surfaces facing one another on opposite sides of the passage. The inner surfaces each include a groove formed therein that is curved between opposite ends of a respective one of the pair of arms so that the curve includes a most distal portion at the central longitudinal axis and the groove is curved proximally from the most distal portion toward the opposite ends of the respective arm. In yet another form, the saddle includes at least one ear on each side of the proximal support surface that is positioned in a respective one of the grooves. The ears are slidably movable along the respective one of the grooves.

In still another form, the saddle includes a pair of ears extending from each side thereof with each of the ears of the side located at an end of the saddle and each of the sides being concavely curved between the pair of ears thereof. In another aspect, the base cap includes a lip extending circumferentially inwardly toward a central axis and around an upper portion of the base cap. The lip defines a passage between an interior recessed surface of base cap and said lip of said base cap. The receiver includes at least one boss extending outwardly from a lower surface of the receptacle. The base cap includes at least one boss recess in the lip that allows the at least one boss to fit through the at least one recess and make contact with the interior recessed surface of the base cap. Upon rotation of the base cap the at least one boss becomes positioned in the passage between the interior recessed surface of the base cap and the lip of the base cap. In another form, a weld seam may be included to secure the receiver to the base cap.

According to another aspect, as the engaging member is tightened the saddle forcibly engages the spacer thereby causing the spacer to fixedly secure the head of the bone anchor in a respective transverse position. The spacer can include at least one edge that is configured to bite into a lower surface of the saddle.

Yet another aspect of the present invention discloses a bone anchor assembly that includes a receiver extending along a central longitudinal axis between a proximal end and an opposite distal end. The receiver includes a distal portion defining a receptacle opening at the distal end and a pair of arms extending from the distal portion along the central longitudinal axis on opposite sides of a passage with the passage opening at opposite sides of the receiver. The receiver includes a bottom surface extending along the passage between the pair of arms and the receptacle opens into the passage. A base cap is included that has an upper surface extending down toward a lower surface. The base cap has a second passage in the lower surface having a first orientation that opens up into an interior surface defined in the base cap. The interior surface includes a head tray having a second orientation in relation to the second passage. The base cap further includes a lip running circumferentially around the upper surface of the base cap defining a third passage between the interior surface and the lip.

A bone anchor is included that has a distal bone engaging portion and a head at a proximal end of the distal bone engaging portion. The head is operable to be positioned in the first orientation such that the head passes through the second passage of the base cap and once placed through the second passage is operable to be positioned in the second orientation such that ends of the head are positioned in the head tray such that the bone anchor can pivot along a transverse plane. A saddle is positioned in the passage of the receiver adjacent to the bottom surface of the receiver. The saddle includes a proximal support surface and a distal surface opposite the proximal support surface.

A spacer is positioned in the receptacle of the receiver such that an upper surface of the spacer is in contact with a lower surface of the saddle and a lower surface of the spacer is in contact with an upper surface of the head. A connecting element extends along a central longitudinal axis and the connecting element is located in the passage and extends through the opposite sides of the receiver. An engaging member is engaged to the pair of arms to secure the connecting element against the proximal support surface of the saddle. Force applied to the saddle is transferred to the spacer which in turn transfers force to the head of the bone anchor thereby preventing the bone anchor from further pivoting in the head tray.

In one form, the receiver includes at least one boss extending outwardly from a lower surface of the receiver. The lip of the base cap includes at least one boss recess that allows the at least one boss to travel downwardly in the base cap to make contact with the interior surface. Upon rotation of the receiver the bosses travel into the third passage between the interior surface and the lip thereby preventing removal of the receiver from the base cap. The receiver and the base cap can also be further connected with a weld seam around outside mating surfaces of the receiver and base cap.

Related features, aspects, embodiments, objects and advantages of the present invention will be apparent from the following description.

BRIEF DESCRIPTION OF THE DRAWINGS

FIG. 22 is a top plan view of the base cap.
FIG. 23 is a bottom plan view of the base cap.
FIG. 24 is a section view along line 24-24 of FIG. 23.

DESCRIPTION OF THE ILLUSTRATED EMBODIMENTS

Figure 1:
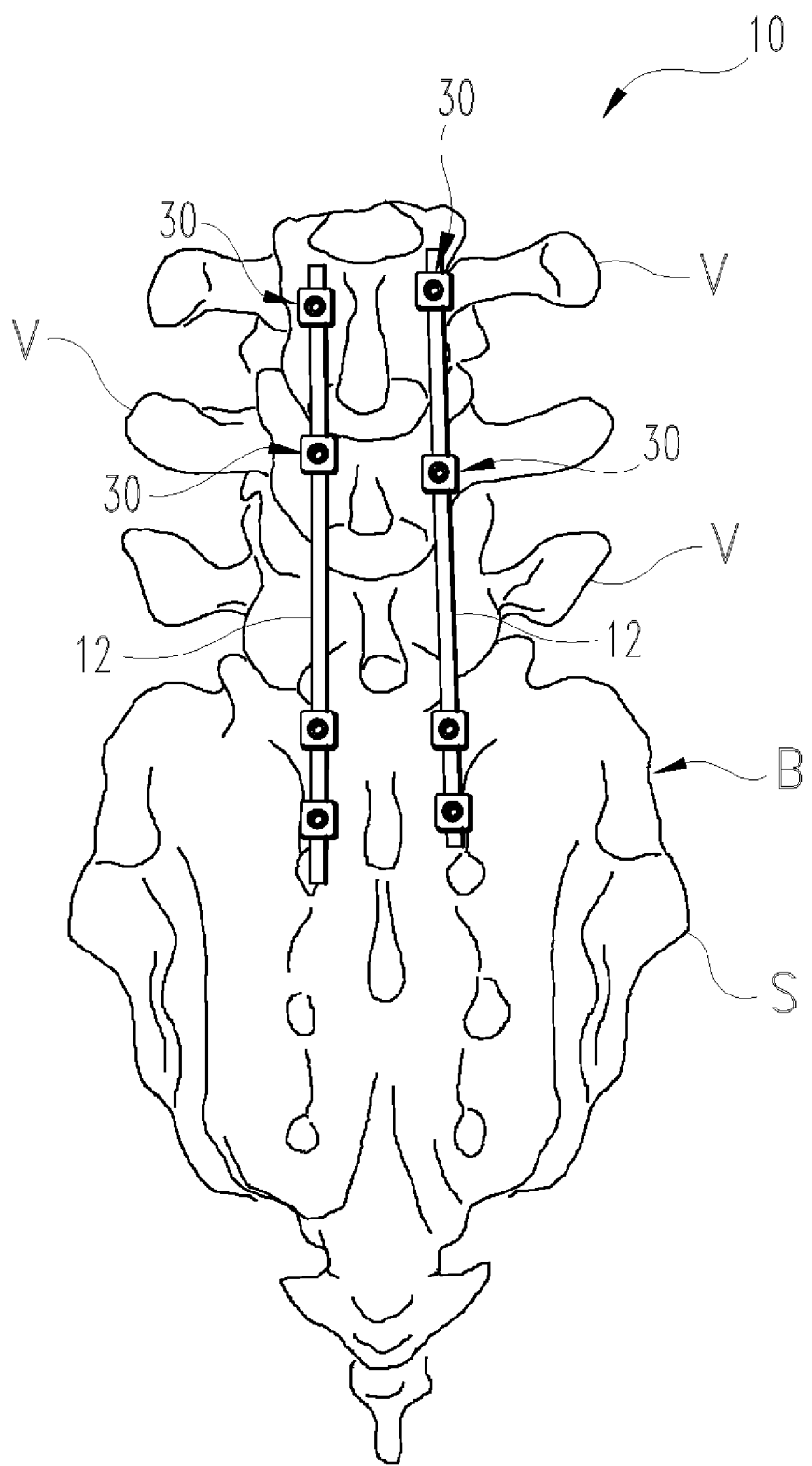
FIG. 1 is a posterior elevation view of a spinal column segment with a spinal implant system engaged thereto.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

FIG. 1 illustrates a posterior spinal implant system 10 located along a spinal column of a patient. Implant system 10 generally includes several bone anchor assemblies 30 with at least one elongated connecting element 12 structured to selectively interconnect two or more bone anchors. Connecting elements 12 may be a spinal rod, plate, bar, or other elongated element having a length to extend between at least two vertebrae. Spinal implant system 10 may be used for, but is not limited to, treatment of degenerative spondylolisthesis, fracture, dislocation, scoliosis, kyphosis, spinal tumor, and/or a failed previous fusion. More specifically, in one embodiment implant system 10 is affixed to posterior elements, such as the pedicles of vertebra V, or other bones B of the spinal column segment, from a posterior approach. Bones B can include the sacrum S and/or one or more of several vertebrae V. Spinal implant system 10 can be engaged to vertebrae of one or more levels of the sacral, lumbar, thoracic and/or cervical regions of the spinal column. Other embodiments contemplate that spinal implant system 10 is engaged along other portions of the spine, such as the anterior, lateral or oblique portions of the vertebrae V. Still other embodiments contemplate applications in procedures other the spinal stabilization procedures.

Figure 2:
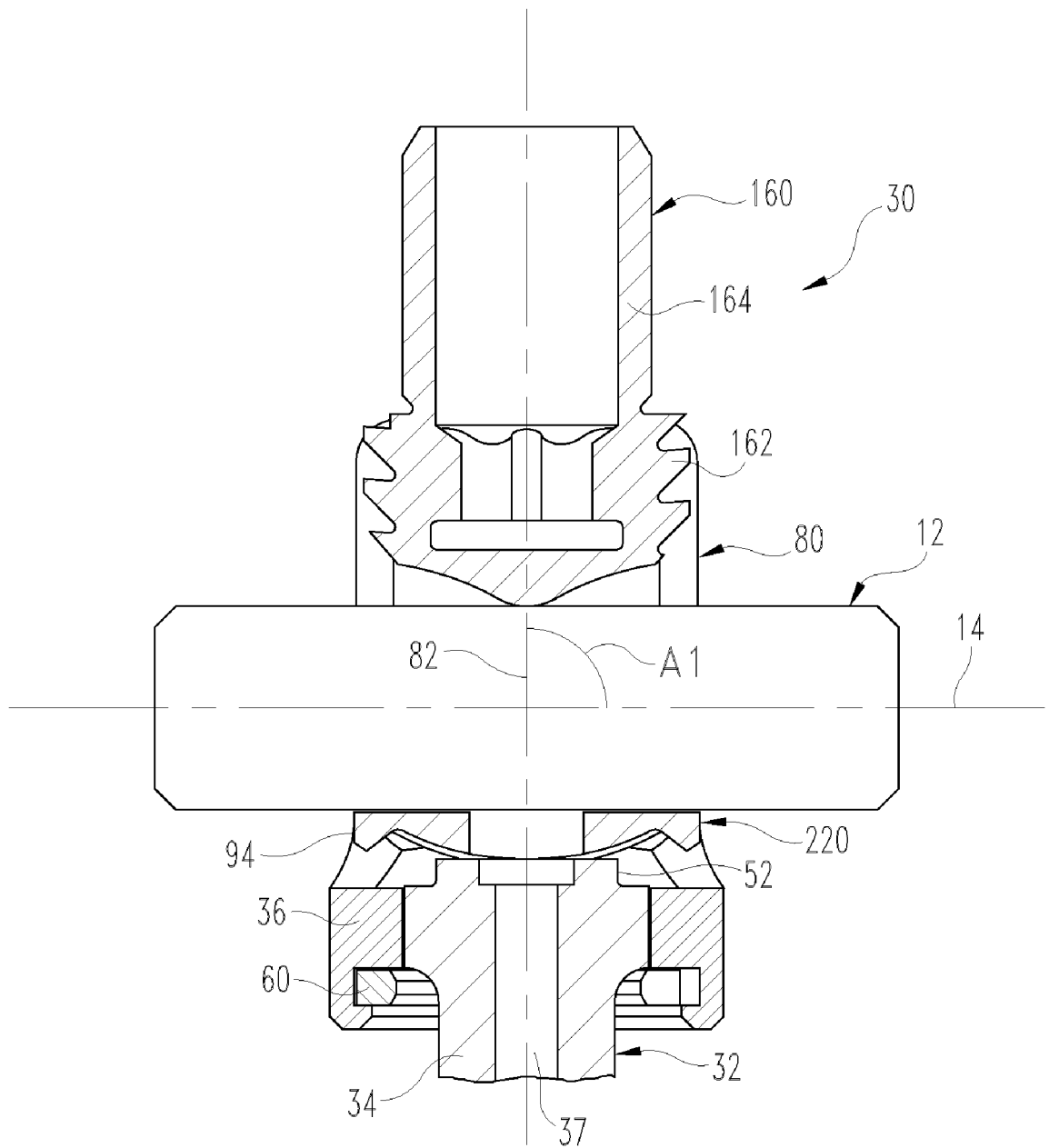
FIG. 2 is a partial sectional view of one embodiment of a bone anchor assembly with the connecting element in a first orientation relative to the bone anchor.
Figure 3:
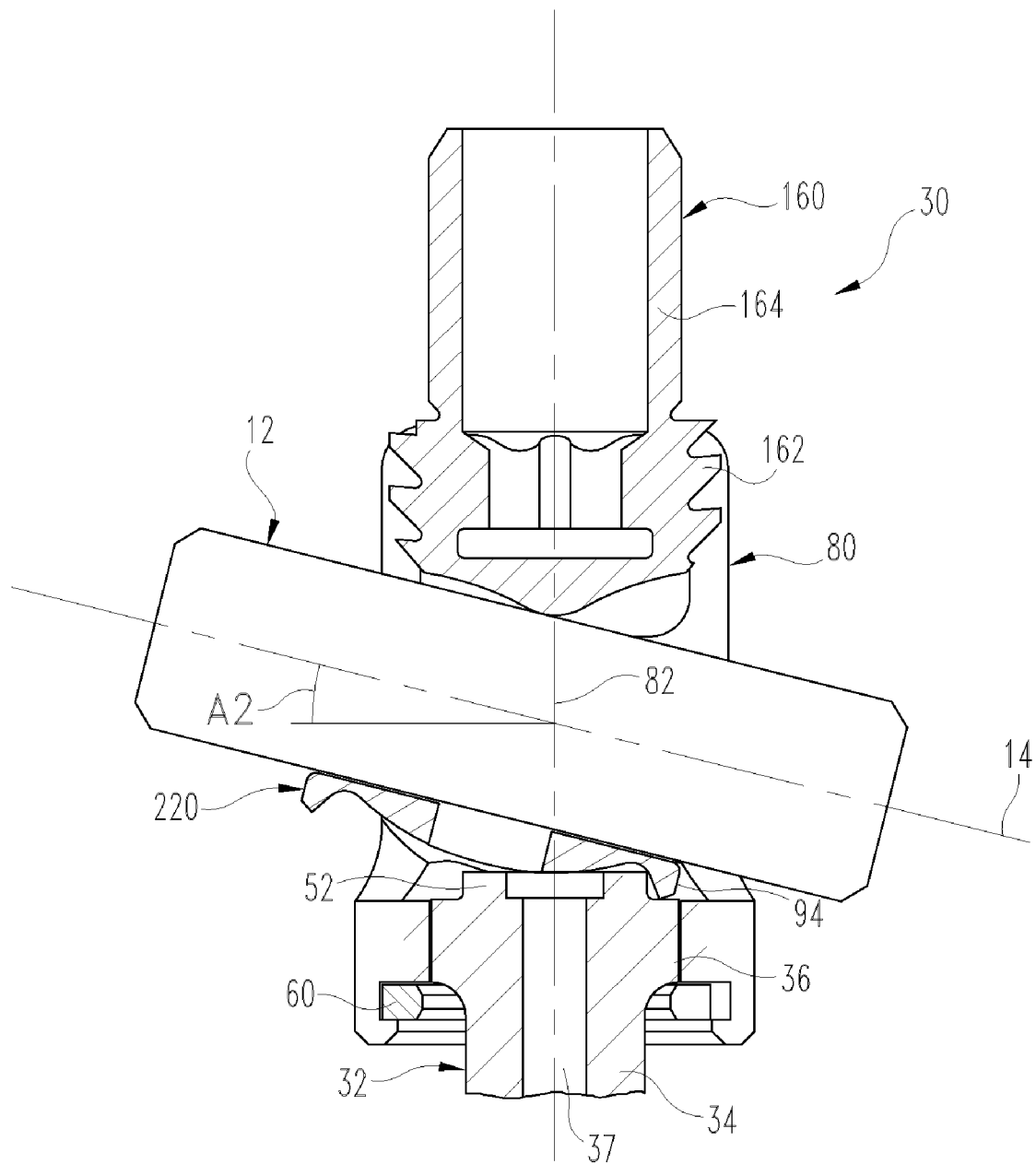
FIG. 3 is a partial sectional view of the bone anchor assembly of FIG. 2 with the connecting element in a second orientation relative to the bone anchor.

Referring to FIGS. 2-3, there is shown a longitudinal section view of a portion of one embodiment of bone anchor assembly 30 and connecting element 12 projecting from opposite sides of the bone anchor assembly 30. Bone anchor assembly 30 includes a bone anchor 32 with a distal bone engaging portion 34 configured for attachment to a vertebra, such as cervical, thoracic, lumbar and/or sacral vertebrae, or other bones or tissues in the body of a patient. Bone anchor assembly 30 also includes a receiver 80 coupled to bone anchor 32 with retaining member 60. Receiver 80 includes a passage 94 extending through opposite sides of receiver 80 that receives connecting element 12 in a transverse orientation to bone anchor 32.

An adjustable saddle 220 is located in receiver 80 between a proximal head 36 of bone anchor 32 and connecting element 12. Saddle 220 supports connecting element 12 in receiver 80 and pivots in a plane defined by the central longitudinal axis 14 of connecting element 12 and a central longitudinal axis 82 of receiver 80. Saddle 220 supports connecting element 12 and maintains a proximal support surface of saddle 220 in contact with connecting element 12 at various orientations of longitudinal axis 14 relative to longitudinal axis 82 that vary from an orthogonal orientation A1, such as shown in FIG. 2, to a maximum angular orientation A2, such as shown in FIG. 3. In one embodiment, angle A2 is 30 degrees from the orthogonal orientation 14' of connecting element 12. Other embodiments contemplate angle A2 ranging from more than 0 degrees to about 45 degrees. The orientation of connecting element 12 and saddle 220 can vary at angle A2 relative to longitudinal axis 82 while the orientation between receiver 80 and bone anchor 32 is maintained in a fixed or substantially fixed relationship. As saddle 220 is pivoted toward the maximum angular orientation, one end of saddle member 220 can project outwardly from passage 94 through the adjacent end of receiver 80, as shown in FIG. 3. Engaging member 160 is engaged to receiver 80 and secures connecting element 12 in receiver 80 against saddle 220 in the selected or desired orientation.

Figure 4:
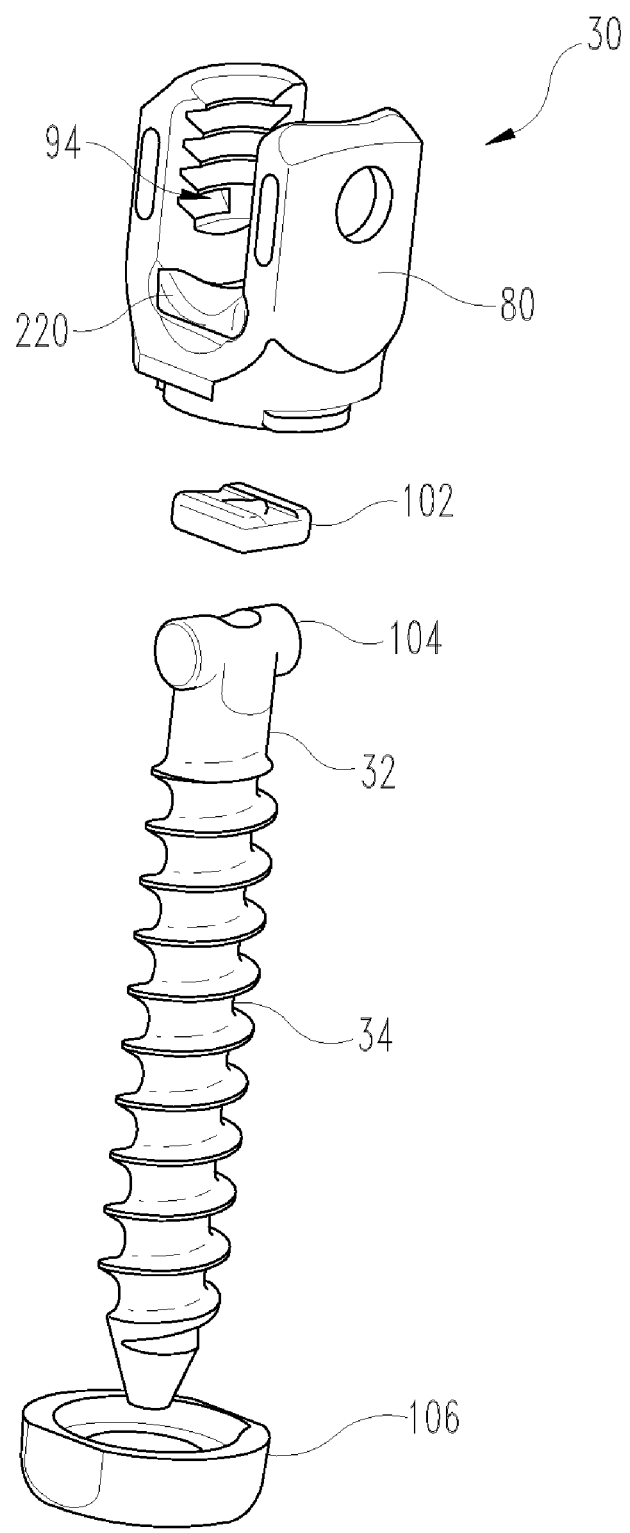
FIG. 4 is a perspective view of another representative bone anchor assembly.

Referring to FIG. 4, wherein like numeral references correspond to similar elements, another representative bone anchor assembly 30 is illustrated without connecting element 12 or engaging member 160. As with the previous form, bone anchor assembly 30 includes a receiver 80 that includes an adjustable saddle 220. Adjustable saddle 220 operates in the same manner as that described in connection with the form illustrated in FIGS. 2 and 3. As described in greater detail below, bone anchor assembly 30 includes a spacer 102 that is received within receiver 80. Bone anchor 32 includes a proximal screw head 104 that is generally circular in shape that extends outwardly horizontally in relation to bone engaging portion 34. A base cap 106 is included that is used to secure the bone anchor 32 and spacer 102 within receiver 80. In this form, the base cap 106 is generally circular in shape and has two opposing flat surfaces that a tool may be engaged with during assembly.

Figure 5:
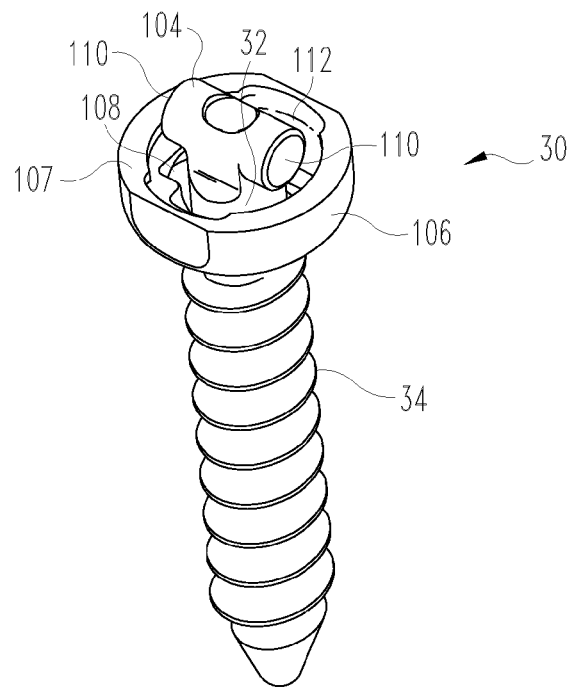
FIG. 5 is a perspective view of a bone anchor and base cap.
Figure 6:
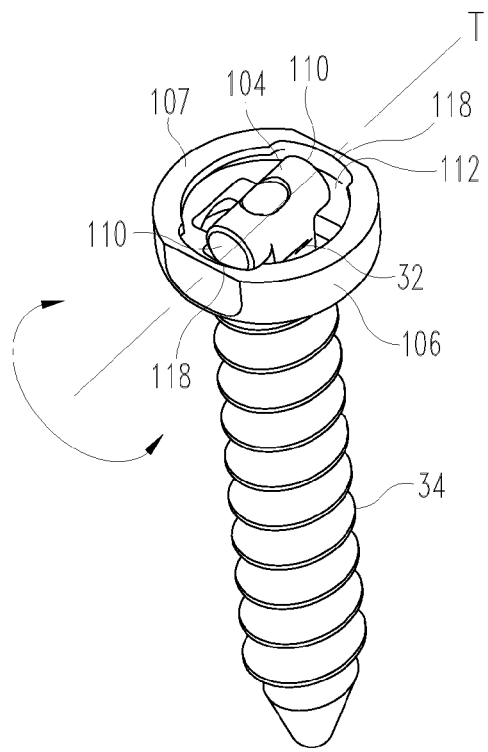
FIG. 6 is a perspective view of the bone anchor and base cap illustrated in FIG. 5.

Referring collectively to FIGS. 5 and 6, during assembly of bone anchor assembly 30 the circular shaped head 104 is inserted through a head receiving aperture or passage 108 located in cap 106. Head passage 108 is sized such that head 104 has enough clearance to fit within cap 106. In this form, head passage 108 has a generally rectangular shape, but other shapes could be used in other forms. As illustrated in FIG. 6, once head 104 is inserted through head passage 108, bone anchor 32 is rotated so that respective ends 110 of head 104 rest within a head tray or receiver 112 included in cap 106. See FIGS. 22 and 24. In this form, bone anchor 32 is rotated approximately 90° in order for head 104 to be received in head tray 112. Head tray 112 is recessed within cap 106 such that a portion of head 104 of bone anchor 32 is located above an upper surface 107 of base cap 106.

As illustrated, once located in head tray 112, bone anchor 32 is able to pivot within base cap 106 along a transverse axis T in relation to base cap 106. In one form, bone anchor 32 is operable to pivot 30° to 45° in both directions in relation to transverse axis T. As it relates to the spinal implant system 10 illustrated in FIG. 1, in this form of bone anchor assembly 30 the saddle 220 provides adjustment of connecting element 12 in the sagittal plane of the spinal column and bone anchor 32, by way of being operable to pivot in cap 106, provides adjustment in the transverse plane of the spinal column. As such, in this representative form bone anchor assembly 30 is configured and operable to provide both sagittal and transverse plane adjustment.

Figure 7:
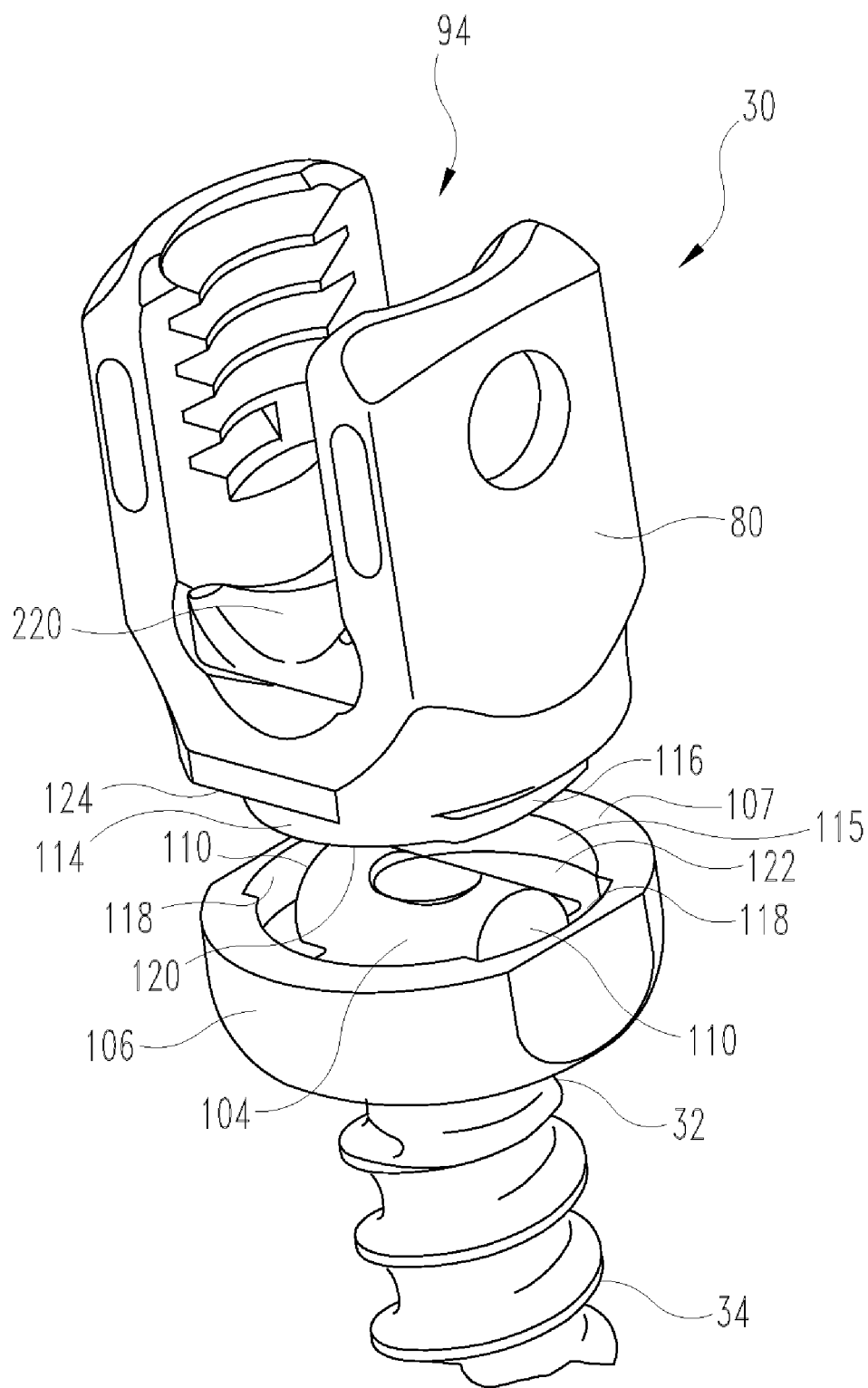
FIG. 7 is a partial perspective view of the bone anchor assembly illustrated in FIG. 4.
Figure 8:
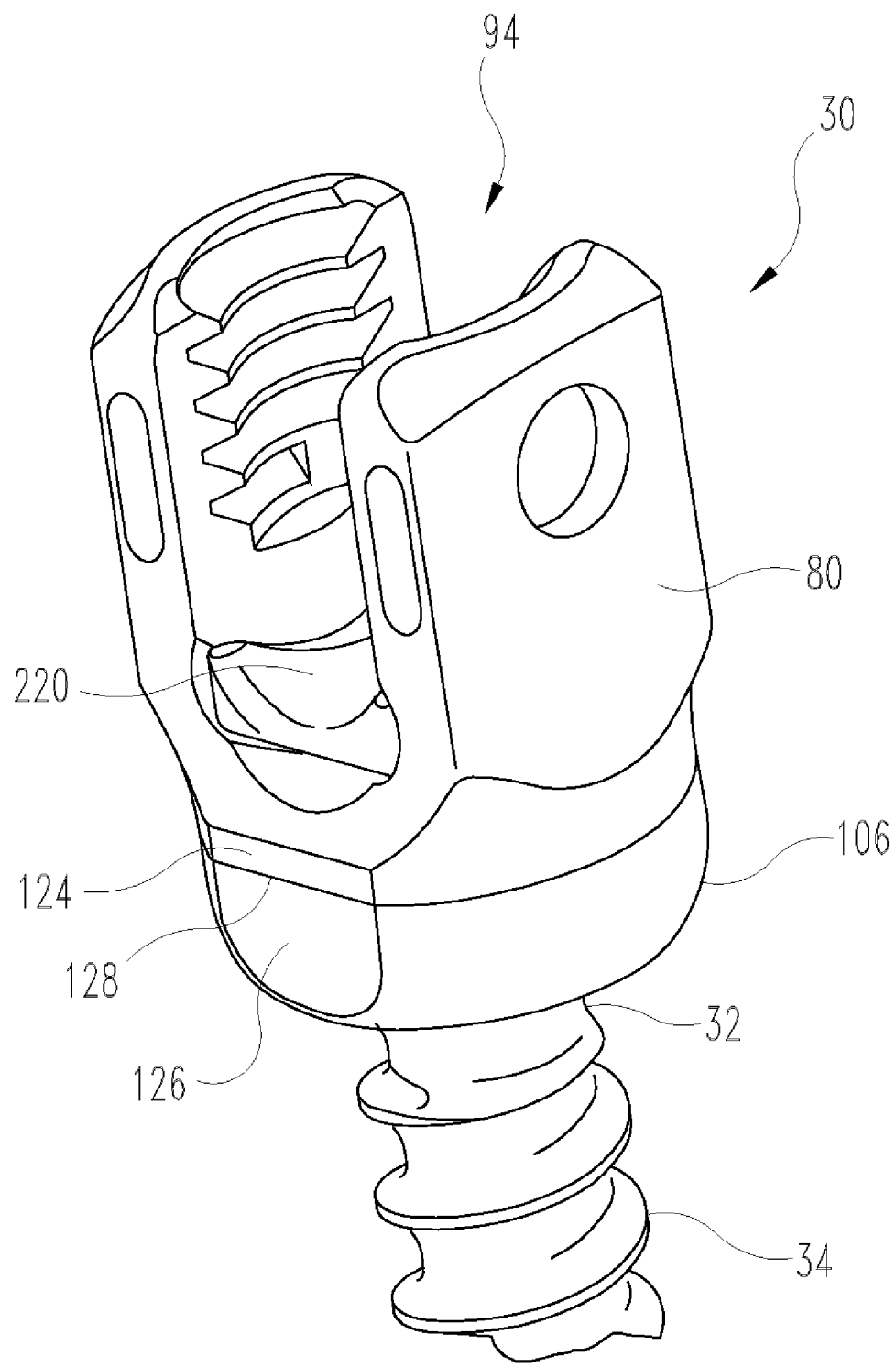
FIG. 8 is another partial perspective view of the bone anchor assembly illustrated in FIG. 4.

Referring collectively to FIGS. 7 and 8, further steps utilized to assemble bone anchor assembly 30 are illustrated. In this form, a lower portion 114 of head 80 includes a boss 116 located on each side of head 80. As illustrated, bosses 116 protrude outwardly from the lower surface 114 of head 80. Base cap 106 includes boss receivers 118 that are formed in the upper surface 107 of base cap 106 so that head 80 can be placed into an interior cavity 115 defined in base cap 106. Boss receivers 118 provide clearance so that bosses 116 can be received by base cap 106. When placed in base cap 106, a lower surface 120 of head 80 makes contact with an inner or interior surface 122 of base cap 106. At this point, head 80 is rotated within base cap 106 thereby locking head 80 on base cap 106. In one form, head 80 is rotated such that flat surfaces 124 of head 80 align with flat surfaces 126 of base cap 106. In an illustrative form, head 80 is rotated approximately 90° to lock head 80 into base cap 106. To further secure head 80 to base cap 106, in one form a weld seam 128 may be included around the mating surfaces of head 80 and base cap 106 to permanently lock the assembly.

During surgery, bone anchor assembly 30 described in connection with FIGS. 4-8 is inserted in the following manner. A driver instrument 300 (see FIG. 27) is first inserted into the head 80. The driver instrument 300 provides torque to the head 80. Head 80 provides torque to the base cap 106 through the weld seam 128. Based cap 106 in turn provides torque to the bone anchor 32. As such, torque is transferred through weld seam 128 in order to deliver the bone engaging portion 34 to a respective location along the spinal column of the patient.

Figure 9:
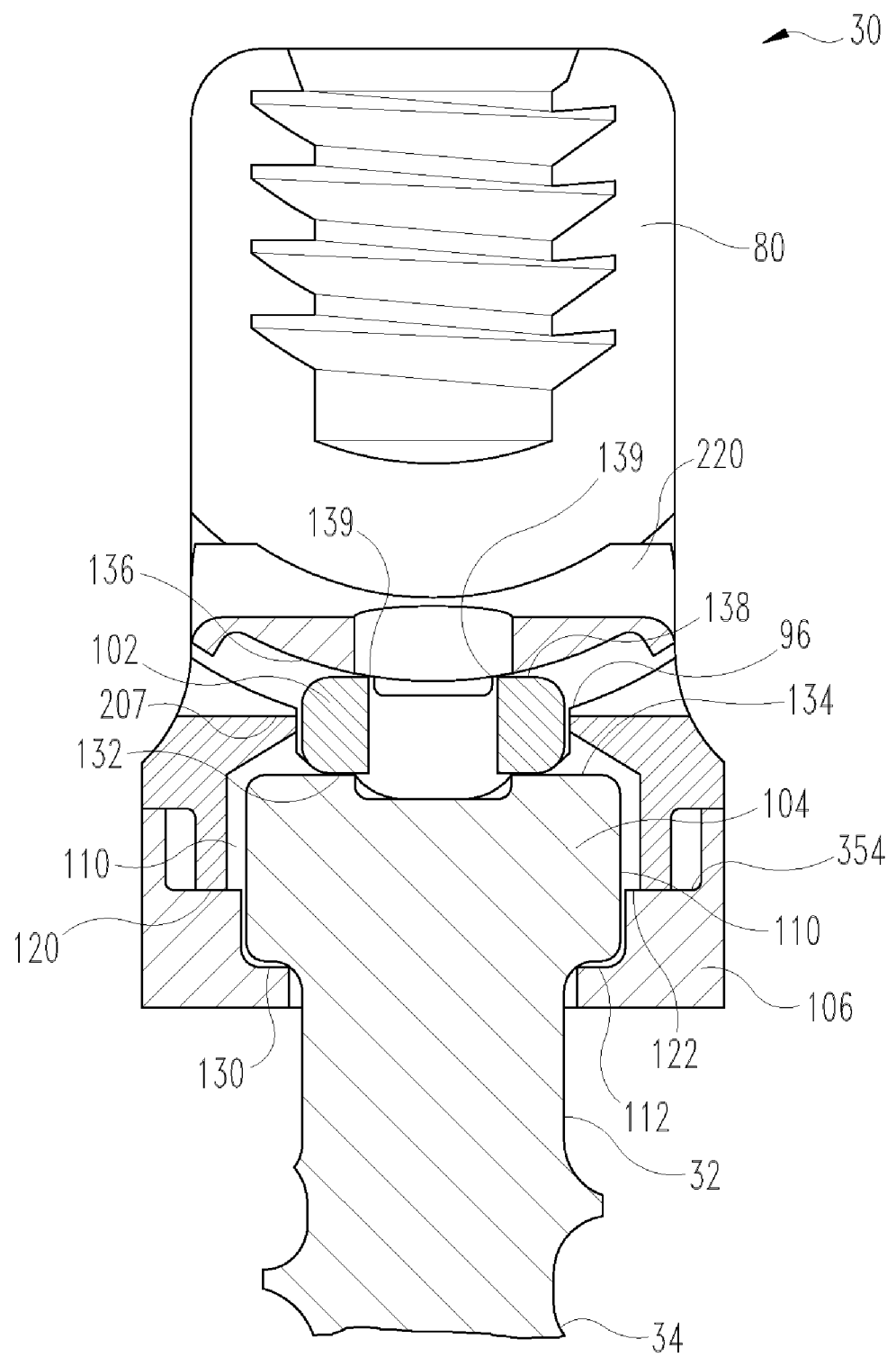
FIG. 9 is a partial sectional view of the bone anchor assembly illustrated in FIG. 4.

Referring to FIGS. 7-9, head 104 of bone anchor 32 has been positioned in head tray 112. Ends 110 of head 104 pivotally rest within a radial recess 130 defined by head tray 112. Positioned between saddle 220 and bone anchor 32 is spacer 102 (see FIG. 9). The upper surface of radial recess 130 can be knurled, serrated, or splined to further help secure head 104 in head tray 112. A lower surface 132 of spacer 102 contacts an upper surface 134 of head 104 and a lower surface 136 of saddle 220 contacts an upper surface 138 of spacer 102. When bone anchor 32 is positioned in the spinal column in the desired transverse plane alignment and connecting element 12 is positioned in saddle 220 in the desired sagittal orientation, engaging member 160 is threaded onto head 80. As engaging member 160 engages connecting element 12 a force is exerted on saddle 220, spacer 102, and head 104. Spacer 102 includes one or more edges 139 that bite into saddle 220 as force is applied to connecting element 12. In one form, saddle 220 is manufactured from a softer material than spacer 102 thereby allowing spacer 102 to bite into saddle 220 during implantation. This helps lock saddle 220 in place thereby preventing any further movement of saddle 220. Further, the force exerted on spacer 102 is also transferred downwardly to head 104 of bone anchor 32. The force exerted by spacer 102 on head 104 also locks bone anchor 32 in its respective transverse orientation or alignment.

Figure 10:
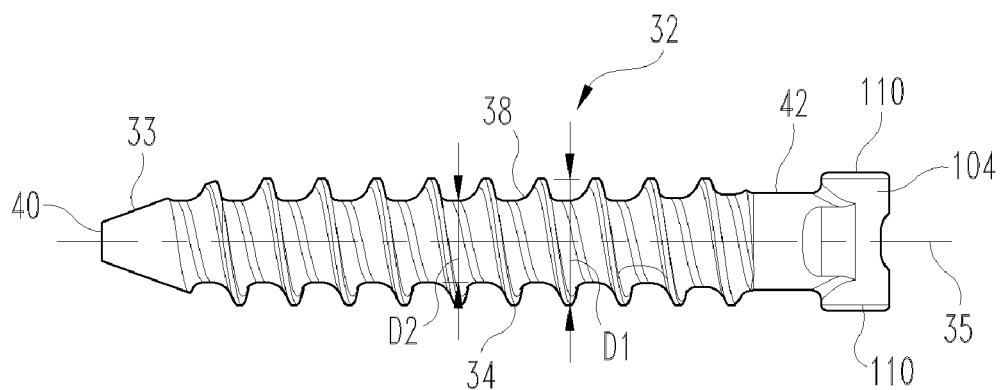
FIG. 10 is a perspective view of the bone anchor illustrated in FIGS. 4-9.

FIG. 10 shows an additional view of bone anchor 32. Bone anchor 32 described herein can be included with bone engaging portion 34 configured as a bone screw, vertebral hook, bone clamp, and or other suitable bone engaging arrangement. Bone anchor 32 includes an elongated bone engaging portion 34 extending from a distal end portion 33 along a central longitudinal axis 35 to a proximal head 104 that is centered on central longitudinal axis 35. Bone engaging portion 34 is shown with an elongated shaft 38 having one or more threads along at least a portion thereof. The threads may be cancellous threads with the shaft sized and configured for implantation into a vertebra or other bone. The threads of bone engaging portion 34 may be self-tapping, self-drilling, continuous, intermittent, of multiple thread forms, or other appropriate configurations. Furthermore, bone anchor 32 may include a lumen 37 as shown in FIGS. 2-3, or be solid. Lumen 37 extends through the proximal and distal ends of anchor 32 for receipt of guidewire and/or injection of material into the bone. One or more fenestrations may be provided along bone engaging portion 34 of bone anchor 32 that communicate with lumen 37.

Bone anchor 32 includes elongated shaft 38 extending proximally and distally along longitudinal axis 35 between head 104 and distal end portion 33. Distal end portion 33 includes a flat distal end 40, and tapers outwardly from distal end 40 along a frusto-conically shaped end portion 33 to a threaded portion of shaft 38. The threaded portion of shaft 38 includes a helical thread with a major diameter D1 and a minor diameter D2 that are constant along a major length of shaft 38 from distal end portion 33 to a transition portion 42 between shaft 38 and head 104. Transition portion 42 includes a smooth and circular outer surface extending around shaft 38 that defines a third diameter D3 that is greater than minor diameter D2 and less than major diameter D1. The helical thread runs out at transition portion 42. Other embodiments contemplate other configurations for the thread profile and shaft 38, including those with varying diameters and profiles along the length of shaft 38.

FIGS. 11-15 show further details of receiver 80. Receiver 80 includes a U-shaped body extending along central longitudinal axis 82 between a distal end 85 and a proximal end 86. Receiver 80 includes a distal connection portion 88 extending proximally from distal end 85, and a pair of arms 90, 92 extending proximally from distal connection portion 88 on opposite sides of longitudinal axis 82 to proximal end 86. Arms 90, 92 define a passage 94 therebetween that opens at opposite sides of arms 90, 92 to receive connecting element 12 in a transverse orientation to longitudinal axis 82. Connection portion 88 includes bosses 116 that extend away from a cylindrical support member 117 that has an outside diameter smaller than that of the outside diameter of arms 90, 92. Cylindrical support member 117 runs substantially parallel with longitudinal axis 82 and terminates at lower surface 120 of receiver 80.

Connection portion 88 also includes a receptacle 96 that opens into passage 94 and extends from passage 94 through distal end 85. Arms 90, 92 also define a proximal opening 98 at proximal end 86 that extends along arms 90, 92 to passage 94. Engaging member 160 is engaged to receiver 80 through the proximal end opening 98 to contact connecting element 12 in passage 94. See e.g. FIGS. 2 and 3. Arms 90, 92 each include a circular recess 100, 102 in the outer side surface 101, 103, respectively, thereof that face opposite directions from one another. Arm 90 also includes oblong recesses 87 in each of the opposite end surfaces 91, 93 thereof. Arm 92 similarly includes oblong recesses 89 in each of the opposite end surfaces 91, 93 thereof. The recesses 87, 89 provide locations in which various tools and instrumentation can be engaged and mounted to receiver 80 to facilitate implantation and maneuvering of bone anchor 30 and connecting element 12 in the patient. End surfaces 91, 93 each are elongated in a longitudinal direction in a parallel orientation to longitudinal axis 82, and extend between the respective outer side surface 101, 103 to the respective inner surface 163, 165 of arms 90, 92 in an orthogonal orientation to longitudinal axis 82. Each of the inner surfaces 163, 165 includes a central concavely curved portion and linear end portions between the respective end surfaces 91, 93. The central concave portion of inner surface 163, 165 defines a thread profile 167 to threadingly engage engaging member 160. Each thread profile 167 extends along longitudinal axis 82 from proximal end 86 of arms 90, 92 to a location adjacent to passage 94 in receiver 80.

Figure 15:
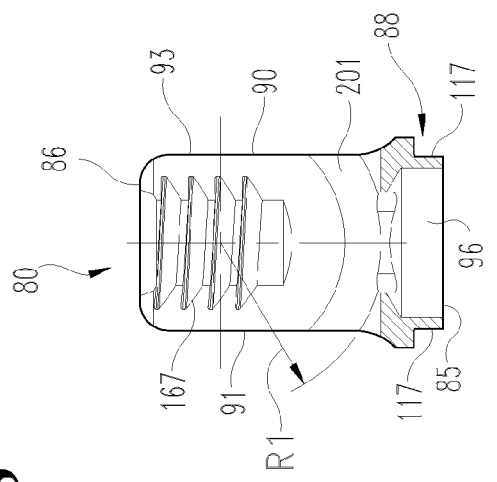
FIG. 15 is a section view along line 15-15 of FIG. 14. \
Figure 11:
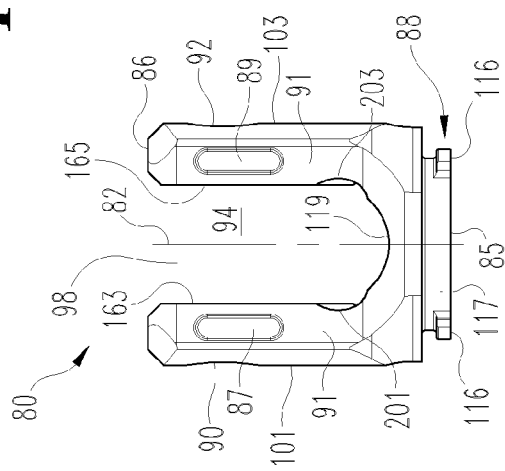
FIG. 11 is an elevation view of a receiver of the bone anchor assembly.
Figure 14:
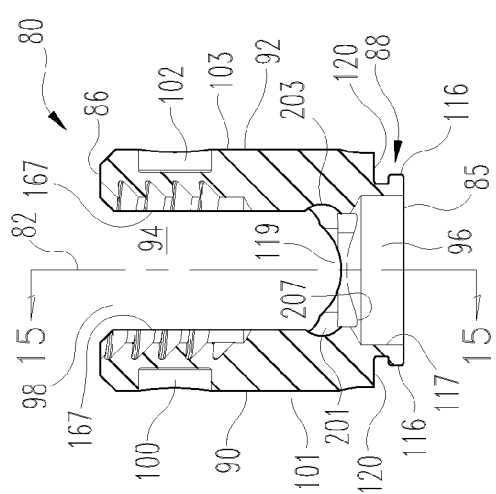
FIG. 14 is a section view along line 14-14 of FIG. 13.
Figure 18:
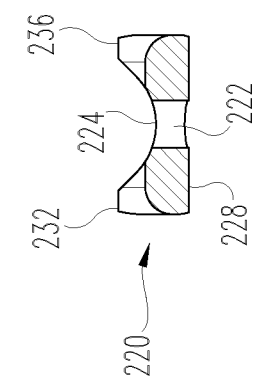
FIG. 18 is a side elevation view of the saddle of FIG. 16.

Receiver 80 includes a bottom surface 119 that extends between inner surfaces 163, 165 of arms 90, 92 along the distal side of passage 94. Receptacle 96 opens through bottom surface 119. In addition, each of the arms 90, 92 includes a groove 201, 203, respectively, formed in the respective inner surface 163, 165 thereof along bottom surface 119. Each groove 201, 203 extends from one of the end surfaces 91 of the respective arm 90, 92 to the other end surface 93 of the respective arm 90, 92. As shown in FIG. 15, each groove 201, 203 is curved between the respective end surfaces of the arm in which it is formed with the distal side of the groove defined by a radius R1 so that the middle of the curved groove is located more distally than the opposite ends of the groove. The distal sides of the grooves 201, 203 intersect receptacle 96 adjacent the middle portions of the grooves 201, 203. Grooves 201, 203 extend from the middle portion thereof so that the opposite ends of grooves 201, 203 are spaced proximally from bottom surface 119 where the groove exits at the opposite end surfaces 91 or end surfaces 93 of the respective arm 90, 92. Grooves 201, 203 are concavely curved in the respective inner surface 163, 165 to form a C-shape as shown in FIG. 15. Saddle 220 is sized and configured to slide in grooves 201, 203 to allow for sagittal adjustment of connecting element 12.

Figure 12:
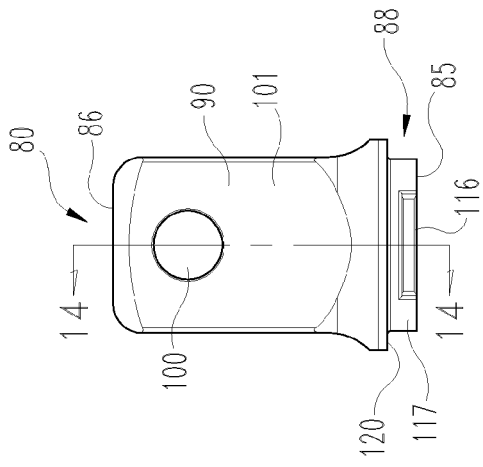
FIG. 12 is a top plan view of the receiver of FIG. 11.
Figure 13:
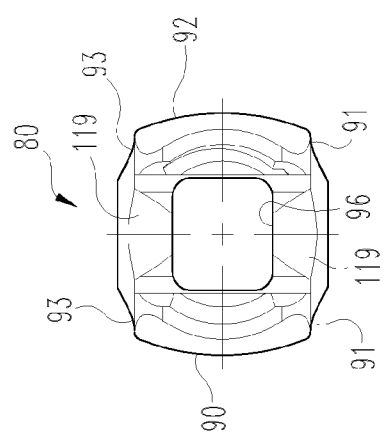
FIG. 13 is a side elevation view of the receiver of FIG. 11.

As shown in FIGS. 9 and 12, receptacle 96 includes a square shaped opening through bottom surface 119 defined by lip 207 extending around the proximal side of receptacle 96. As previously set forth, spacer 102 is sized to extend through the square-shaped opening to contact lower portion 138 of saddle 220 positioned along bottom surface 119. As previously set forth, edges 139 of spacer 102 are configured to bite into saddle 220 when connecting element 12 is tightened onto bone anchor assembly 30.

Figure 17:
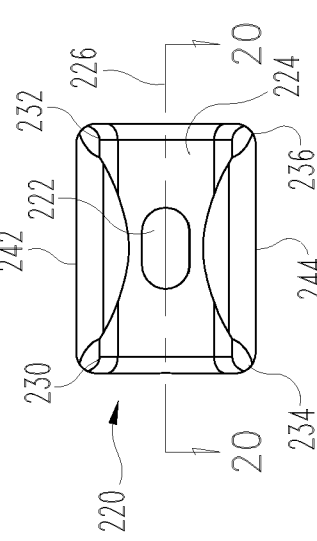
FIG. 17 is a top plan view of the saddle of FIG. 16.
Figure 16:
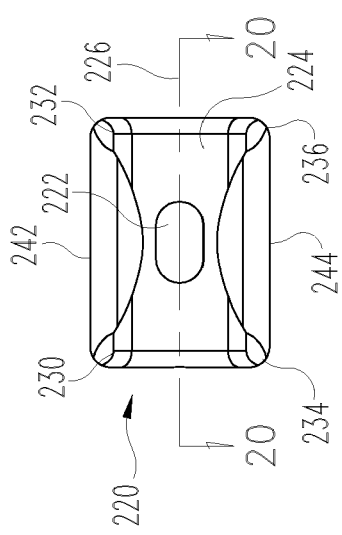
FIG. 16 is a perspective view of a saddle comprising a portion of the bone anchor assembly.
Figure 21:
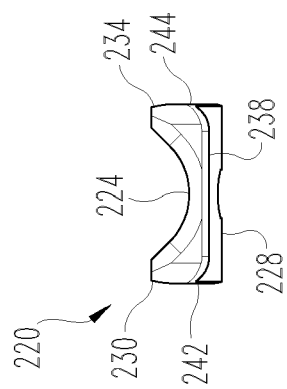
FIG. 21 is a section view along line 21-21 of FIG. 20.

FIGS. 16-21 show various view of saddle 220. Saddle 220, as shown in FIGS. 2-3 and 4-9, is positioned in receiver 80 between connecting element 12 and spacer 102. Saddle 220 includes a body with a rectangular shape when saddle 220 is viewed in a proximal to distal direction, as shown in FIG. 17. Saddle 220 extends along a longitudinal axis 226 between opposite ends, and includes an oblong hole 222 extending through a center thereof between upper and lower surfaces thereof. Hole 222 aligns with lumen 37 of bone anchor 32. The oblong shape of hole 222 allows at least a portion of hole 222 to align with lumen 37 even if saddle 220 is pivoted to a non-centered position in receiver 80. Saddle 220 includes a proximal support surface 224 against which connecting element 12 is positioned. Proximal support surface 224 is linear in a direction paralleling longitudinal axis 226 as shown in FIG. 22, and is concavely curved orthogonally to longitudinal axis 226 as shown in FIGS. 21 and 23. The shape of proximal support surface 224 matches the shape of the portion of the outer surface of connecting element 12 positioned thereagainst.

Figure 20:
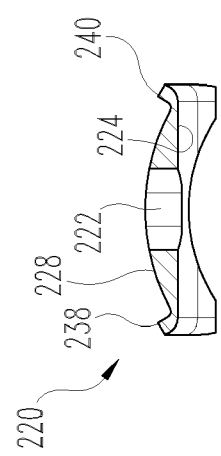
FIG. 20 is a section view along line 20-20 of FIG. 19.
Figure 19:
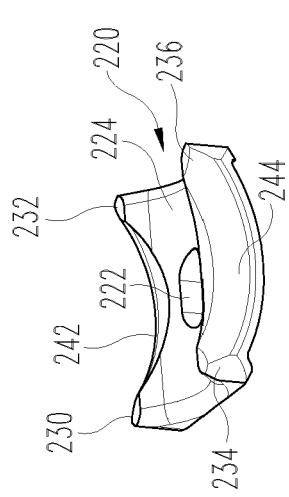
FIG. 19 is an end elevation view of the saddle of FIG. 16.

Saddle 220 includes a distal surface 228 opposite proximal surface 224. Distal surface 228 is convexly curved along longitudinal axis 226 as shown in FIGS. 20 and 22, and is linear between the opposite sides of saddle 220, as shown in FIGS. 21 and 23. Distal surface 228 contacts and is supported by platform 52 of head 36 of bone anchor 32. The convexly curved distal surface 228 facilitates pivoting movement of saddle 220 in the plane that includes longitudinal axis 82 of receiver 80 and longitudinal axis 14 of connecting element 12. In addition, saddle 220 includes ears 230, 232, 234, 236 extending outwardly from proximal support surface 224 that are received in respective ones of the grooves 118, 120 of receiver 80. Ears 230, 232 are positioned in and translate along groove 118, and ears 234, 236 are positioned in and translate along groove 120 as saddle 220 pivots in receiver 80 in the plane defined by longitudinal axis 82 of receiver 80 and longitudinal axis 14 of connecting element 12. Ears 230, 232, 234, 236 maintain saddle 220 within receiver 80 along a path defined by grooves 201, 203 and prevent saddle 220 from pivoting or twisting to an undesired orientation in receiver 80.

Saddle 220 also includes a first tooth 238 at one end thereof that extends between ears 230, 234 and projects distally from distal surface 228, and saddle 220 includes a second tooth 240 at the opposite end thereof that extends between ears 232, 236 and projects distally from distal surface 228. Saddle 220 includes a first elongate side 242 extending between ears 230, 232 with a proximal side that is concavely curved between ears 230, 232 and an opposite convexly curved distal side between ears 230, 232. Saddle 220 also includes a second elongate side 244 extending between ears 234, 236 with a proximal side that is concavely curved between ears 234, 236 and an opposite convexly curved distal side between ears 234, 236. The curvature of sides 242, 244 corresponds to the curvature of the respective groove 201, 203 so that saddle 220 extends across bottom surface 116 of receiver 80 into the grooves 201, 203. Convexly curved distal surface 228 contacts rails 54 of platform 52 and slides along rails 54 as saddle 220 translates in grooves 201, 203. When saddle 220 is sufficiently pivoted in receiver 80 to a maximum angle A2, one of the first and second teeth 238, 240 contacts an adjacent side of platform 52 to prevent further pivoting movement of saddle 220 in receiver 80, as shown in FIG. 3.

Referring to FIGS. 2-3, engaging member 160 is movably engaged to arms 90, 92 of receiver 80 through the proximal end opening 98 of receiver 80. Engaging member 160 is movable toward passage 94 by threading it along arms 90, 92 of receiver 36 to contact connecting element 12 and direct connecting element 12 into receiver 80 and into engagement with proximal support surface 224 of saddle 220, which in turn moves and/or forces distal surface 228 of saddle 220 into contact with platform 56 of anchor 32, securing connecting element 12 and anchor 32 to one another and securing anchor 32 against retaining member 60 of receiver 80. In the illustrated embodiment, engaging member 160 is a set screw type element with an externally threaded body 162 that threadingly engages inner threads provided along arms 90, 92. Other embodiments contemplate an engaging member in the form of a nut, cap, or combination of nut and setscrew. In still other embodiments, engaging member 160 engages receiver 80 in a non-threaded manner, such as a friction fit, interference fit, or bayonet lock. Engaging member 160 also includes a proximal break-off portion 164 extending from body 162 to facilitate engagement of engaging member 160 to receiver 80 and in the application of sufficient force to secure the assembly of connecting element 12 against saddle 220 and saddle 220 against anchor 32. Break-off portion 164 is severed upon application of a threshold torque that provides the desired level of fixation of anchor assembly 30.

FIGS. 22-24 show various views of base cap 106. As illustrated, in this form base cap 106 has a generally circular shape with two opposing flat surfaces 350. Head tray 112 is located along a longitudinal axis 352 of base cap 106. In this form, head tray 112 has a semi-circular shape so that the end portions 110 of head 104 can pivot or rotate in head tray 112. Head receiving passage 108 has a generally rectangular shape in this form and is centrally located in base cap 106. Base cap 106 further includes a lower recessed interior surface 354 that makes contact with lower surface 120 of head 80 when base cap 106 is connected with head 80. Further, base cap 106 includes an L-shaped lip 356 defined partially by upper surface 107 that protrudes inwardly and runs circumferentially around upper surface 107 of base cap 106. A pair of lip recesses or boss receivers 118 is included on opposing sides of lip 356 along longitudinal axis 352. As previously set froth, boss receivers 118 provide a clearance for bosses 116 of head 80 (see FIG. 7). Once bosses 116 are positioned in boss receivers 118 and the lower surface 120 of head 80 makes contact with lower recessed interior surface 354 of base cap 106, head 80 is rotated approximately 90° in one form such that bosses 116 become positioned under lip 356 thereby retaining head 80 in base cap 106.

Figures 25, 26:
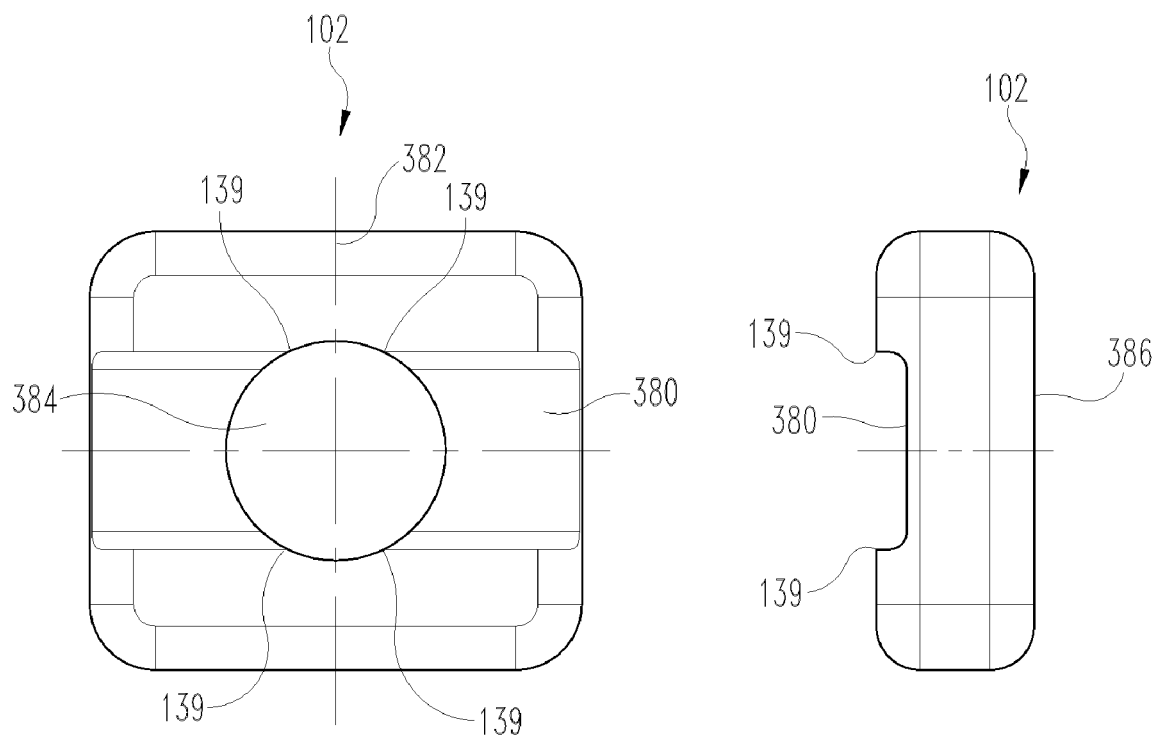
FIG. 25 is a top plan view of a spacer.
FIG. 26 is a side plan view of the spacer.

FIGS. 25 and 26 show two view of spacer 102. Spacer 102 is generally rectangular in shape in this form and includes a recessed channel 380 running along a horizontal axis 382 of spacer 102. A spacer passage 384 is included in a central portion of spacer 102. As previously set forth, spacer 102 includes a plurality of edges 139 that are configured to bite into saddle 220 when engaging member 160 is tightened down onto connecting element 12 once positioned accordingly in head 80. A lower surface 386 of spacer 102 contacts screw head 104 when engaging member 160 is tightened down onto connecting element 12 thereby securely holding screw head 104 in position within head 80.

Figure 27:
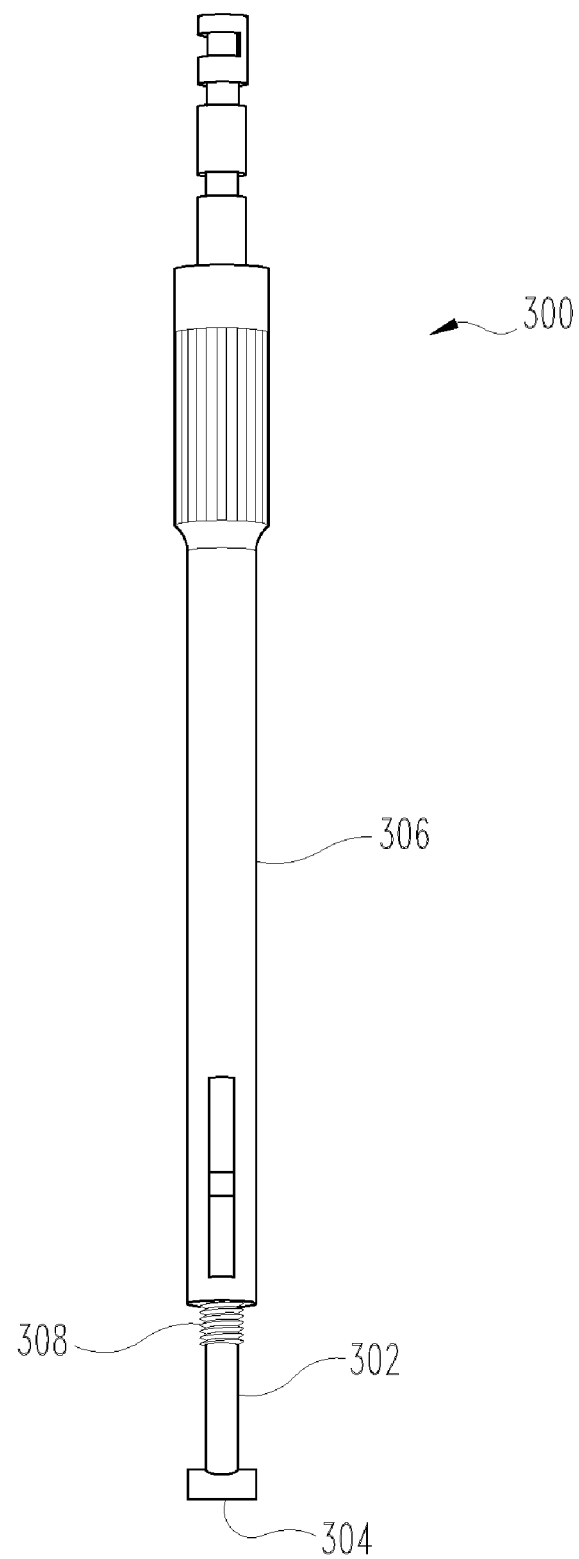
FIG. 27 is a perspective view of a driving tool for inserting a bone anchor assembly into bone.

FIG. 27 shows a driver instrument 300 that can be used to insert and drive the anchor assemblies herein into bone. Driver instrument 300 includes an inner shaft 302 with a distal, cylindrically shaped foot 304 that is elongated along an axis transverse to the longitudinal axis of the instrument to fit within passage 94 of anchor 30 against saddle 220. Driver instrument 300 also includes an outer tubular member 306 positioned around inner shaft 302. Tubular member 306 includes a distal collar 308 spaced proximally from foot 304. Tubular member 306 is rotatable relative to inner shaft 302 to threadingly engage collar 308 with arms 90, 92 of receiver 80 with foot 304 in receiver 80, and press foot 304 against saddle 220 to secure it against head 104 of bone anchor 32. The anchor assembly 30 can then be rotated and threaded into the bone as a rigid, assembled construct with driver instrument 300.

As previously set forth, as engaging member 160 is threaded down on connecting element 12, connecting element 12 exerts a force on the saddle 220. The saddle 220 in turn exerts a force on the upper surface of spacer 102 since at least a portion of spacer 102 extends through receptacle 96 into passage 94. The lower surface of spacer 102 will then exert a force on head 104. Thus, engaging member 160 locks connecting element 12 in place within saddle 220 of receiver 80 along a predetermined sagittal plane and spacer 102 locks head 104 in a predetermined transverse plane. In addition, edges 139 of spacer 102 can bite into saddle 220 to further help secure saddle 200 in its relative position.

The bone anchor assemblies discussed herein allow adjustment of the angle of the saddle and thus the angle of the connecting element extending through the saddle in a single plane defined by the longitudinal axis of the connecting element and the longitudinal axis of the receiver. The bone anchor assemblies provide a two-piece construct for the receiver and the bone anchor that forms a rigid or semi-rigid bone anchor assembly when the receiver is assembled with the bone anchor while limiting angulation of the saddle in a particular plane. The two piece construct allows the receiver and bone anchor to be comprised of different materials suitable for the expected loading of the components. For example, the receiver can be made from a higher strength material than the material for the bone anchor so that the splaying and other deformations of the receiver can be limited by the higher strength material and so that the side of the receiver can be minimized to limit intrusiveness into the surrounding tissue post-implantation.

Materials for the anchors, receivers, saddles and engaging members disclosed herein can be chosen from any suitable biocompatible material, such as titanium, titanium alloys, cobalt-chromium, cobalt-chromium alloys, or other suitable metal or non-metal material. Connecting element 12 can be made from the same material as one or more of the components of the anchor assembly to which it is engaged, or from a different material. For example, connecting element 12 can be made from PEEK, plastic, titanium or titanium alloy, cobalt-chrome, composite material, or other material that is the same or different from the material of one or more components of the anchor assembly to which is engaged. The anchor assemblies can be sized for placement at any level of the spine and for engagement with any bony portion of the spine. In one particular embodiment, the anchor assemblies are engaged to pedicles of the vertebrae. Of course, it is understood that the relative size of the components of the anchor assemblies can be modified for the particular vertebra (e) to be instrumented and for the particular location or structure of the vertebrae to which the anchor assembly will be engaged.

Although various embodiments have been described as having particular features and/or combinations of components, other embodiments are possible having a combination of any features and/or components from any of embodiments as discussed above. As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof. Furthermore, the terms "proximal" and "distal" refer to the direction closer to and away from, respectively, an operator (e.g., surgeon, physician, nurse, technician, etc.) who would insert the medical implant and/or instruments into the patient. For example, the portion of a medical instrument first inserted inside the patient's body would be the distal portion, while the opposite portion of the medical device (e.g., the portion of the medical device closest to the operator) would be the proximal portion.

While the invention has been illustrated and described in detail in the drawings and foregoing description, the same is to be considered as illustrative and not restrictive in character, it being understood that all changes and modifications that come within the spirit of the invention are desired to be protected.

What is claimed is:

1. A bone anchor assembly, comprising:
a receiver extending along a central longitudinal axis between a proximal end and an opposite distal end, said receiver including a distal portion defining a receptacle opening at said distal end and a pair of arms extending from said distal portion along said central longitudinal axis on opposite sides of a passage, wherein a lower outside surface of said receiver includes a pair of bosses spaced apart from one another on opposite sides of said receiver, said bosses protruding outwardly from said lower outside surface and extending parallel to one another;

a base cap including an upper surface extending to a lower surface, said upper and lower surfaces being parallel to one another, said lower surface including an inner surface defining a generally rectangular shaped second passage opening into an interior recessed surface in relation to said upper surface, wherein said base cap further includes a lip extending inwardly from said inner surface toward said upper surface and a central axis of said bone cap that defines a passageway between said lip and said interior recessed surface, wherein said lip includes a pair of spaced apart recessed portions in communication with said passageway configured for disposal of said bosses, the base cap being configured to be connected with a second lower surface of said receiver such that said bosses are positioned in said recessed portions, wherein said interior recessed surface includes a head tray; and a bone anchor including a distal bone engaging portion and a head at a proximal end of said distal bone engaging portion, said head comprising a generally circular shape extending outwardly and horizontally in relation to said bone engaging portion, said head being configured to be received in said base cap through said second passage when said head is positioned in a first orientation and when said bone anchor is rotated to a second orientation said head is configured to pivotally rest in said head tray.

2. The bone anchor assembly of claim 1, further comprising a saddle positioned in said passage of said receiver adjacent to a bottom surface of said receiver, said saddle including a proximal support surface and a distal surface opposite said proximal support surface.

3. The bone anchor assembly of claim 2, further comprising a spacer positioned in said receptacle between an upper surface of said head of said bone anchor and a lower surface of said saddle.

4. The bone anchor assembly of claim 3, wherein said spacer includes at least one edge operable to bite into a lower surface of said saddle to secure said saddle in a respective location within said receiver.

5. The bone anchor assembly of claim 2, wherein said saddle is movable in said receiver so that said support surface parallels a longitudinal axis of a connecting element in orientations of said longitudinal axis of said connecting element that vary up to 30 degrees from an orthogonal orientation of said longitudinal axis of said connecting element with said central longitudinal axis of said receiver.

6. The bone anchor assembly of claim 1, wherein upon rotation of said receiver, said bosses become positioned in said passageway.

7. The bone anchor assembly of claim 1, further comprising a weld seam securing said receiver to said base cap.

8. A bone anchor assembly, comprising:
a receiver extending along a central longitudinal axis between a proximal end and an opposite distal end, said receiver including a distal portion defining a square shaped receptacle opening at said distal end and a pair of arms extending from said distal portion along said central longitudinal axis on opposite sides of a passage, said receiver including a bottom surface extending along said passage between said pair of arms, wherein said passage opens at opposite sides of said receiver between said pair of arms and said receptacle opens into said passage through said bottom surface;

a base cap extending between an upper surface and a lower surface, said upper and lower surfaces being parallel to one another, said base cap having a second passage including a generally rectangular shape located in a central portion of said base cap located in a first orientation and a head tray having two opposing recessed members located in a second orientation in relation to said second passage;

a bone anchor including a distal bone engaging portion and a head at a proximal end of said distal bone engaging portion, said head comprising a generally circular shape extending outwardly and horizontally in relation to said bone engaging portion, said head being configured to be received in said base cap through said second passage when said head is positioned in said first orientation and when said bone anchor is rotated to said second orientation said head is configured to pivotally rest along a transverse axis in said head tray;

a rectangular saddle positioned in said passage of said receiver adjacent to said bottom surface of said receiver, said saddle including a proximal support surface and a distal surface opposite said proximal support surface; a spacer positioned between said saddle and said head of said bone anchor inside said receptacle of said receiver;

a connecting element extending along a central longitudinal axis, said connecting element being located in said passage and extending through said opposite sides of said receiver; and an engaging member engaged to said pair of arms to secure said connecting element against said proximal support surface of said saddle, wherein said saddle engages said receiver and is limited to movement in said receiver in a single plane defined by said central longitudinal axis of said receiver and said central longitudinal axis of said connecting element while said bone engaging portion remains in said first orientation.

9. The bone anchor assembly of claim 8, wherein said saddle is movable in said receiver so that said support surface parallels said longitudinal axis of said connecting element in orientations of said longitudinal axis of said connecting element that vary up to 30 degrees from an orthogonal orientation of said longitudinal axis of said connecting element with said central longitudinal axis of said receiver.

10. The bone anchor assembly of claim 8, wherein:
said pair of arms include inner surfaces facing one another on opposite sides of said passage;
said inner surfaces each include a groove formed therein that is curved between opposite ends of a respective one of said pair of arms so that said curve includes a most distal portion at said central longitudinal axis and said groove is curved proximally from said most distal portion toward said opposite ends of said respective arm; and
said saddle including at least one ear on each side of said proximal support surface that are positioned in a respective one of said grooves, said ears being slidably movable along said respective one of said grooves.

11. The bone anchor assembly of claim 10, wherein said saddle includes a pair of ears extending from each side thereof with each of said ears of said side located at an end of said saddle and each of said sides is concavely curved between said pair of ears thereof.

12. The bone anchor assembly of claim 8, wherein said base cap includes a lip extending circumferentially inwardly toward a central axis and around an upper portion of said base cap, wherein said lip defines a passage between an interior recessed surface of said base cap and said lip of said base cap.

13. The bone anchor assembly of claim 12, wherein said receiver includes at least one boss extending outwardly from a lower surface of said receptacle, wherein said base cap includes at least one boss recess in said lip that allows said at least one boss to fit through said at least one recess and make contact with said interior recessed surface of said base cap, wherein upon rotation of said base cap said at least one boss becomes positioned in said passage between said interior recessed surface of said base cap and said lip of said base cap.

14. The bone anchor assembly of claim 13, further comprising a weld seam securing said receiver to said base cap.

15. The bone anchor assembly of claim 8, wherein as said engaging member is tightened said saddle forcibly engages said spacer thereby causing said spacer to fixedly secure said head of said bone anchor in a transverse position.

16. The bone anchor assembly of claim 15, wherein said spacer includes at least one edge that is configured to bite into a lower surface of said saddle.

17. A bone anchor assembly, comprising:
- a receiver extending along a central longitudinal axis between a proximal end and an opposite distal end, said receiver including a distal portion defining a receptacle defining a square shaped opening at said distal end and a pair of arms extending from said distal portion along said central longitudinal axis on opposite sides of a passage with said passage opening at opposite sides of said receiver, said receiver including a bottom surface extending along said passage between said pair of arms, wherein said receptacle opens into said passage;
- a base cap having an upper surface extending down toward a lower surface, said upper and lower surfaces being parallel to one another, said base cap having an inner surface defining a generally rectangular shaped second passage in said lower surface having a first orientation that opens up into an interior surface defined in said base cap, said interior surface including a head tray having a second orientation in relation to said second passage, said base cap including a lip running circumferentially around said upper surface of said base cap defining a third passage between said interior surface and said lip, said lip extending inwardly from said inner surface toward said upper surface and a central axis of said bone cap;
- a bone anchor including a distal bone engaging portion and a head at a proximal end of said distal bone engaging portion, said head comprising a generally circular shape extending outwardly and horizontally in relation to said bone engaging portion, said head being operable to be positioned in said first orientation such that said head may pass through said second passage of said base cap and once placed through said second passage being operable to be positioned in said second orientation such that ends of said head are positioned in said head tray such that said bone anchor can pivot along a transverse plane;
- a rectangular saddle positioned in said passage of said receiver adjacent to said bottom surface of said receiver, said saddle including a proximal support surface and a distal surface opposite said proximal support surface;
- a spacer positioned in said receptacle of said receiver such that an upper surface of said spacer is in contact with a lower surface of said saddle and a lower surface of said spacer is in contact with an upper surface of said head;
- a connecting element extending along a central longitudinal axis, said connecting element being located in said passage and extending through said opposite sides of said receiver; and
- an engaging member engaged to said pair of arms to secure said connecting element against said proximal support surface of said saddle, wherein force applied to said saddle is transferred to said spacer which in turn transfers force to said head of said bone anchor thereby preventing said bone anchor from further pivoting in said head tray.

18. The bone anchor assembly of claim 17, wherein said receiver includes at least one boss extending outwardly from a lower surface of said receiver, wherein said lip of said base cap includes at least one boss recess that allows said at least one boss to travel downwardly in said base cap to make contact with said interior surface, wherein upon rotation of said receiver said bosses travel into said third passage between said interior surface and said lip thereby preventing removal of said receiver from said base cap.

19. The bone anchor assembly of claim 18, wherein said receiver and said base cap are further connected with a weld seam around outside mating surfaces of said receiver and base cap.

* * * * *